United States Patent [19]

Greco

[11] 3,984,466
[45] *Oct. 5, 1976

[54] HYDROLYSIS OF 3,5-DIAMINO BENZOIC ACID TO PRODUCE ALPHA-RESORCYLIC ACID

[75] Inventor: Nicholas P. Greco, Edgewood, Pa.

[73] Assignee: Koppers Company, Inc., Pittsburgh, Pa.

[ * ] Notice: The portion of the term of this patent subsequent to Jan. 21, 1992, has been disclaimed.

[22] Filed: Jan. 17, 1975

[21] Appl. No.: 542,008

Related U.S. Application Data

[63] Continuation-in-part of Ser. No. 267,525, June 29, 1972, Pat. No. 3,862,246, which is a continuation-in-part of Ser. No. 16,545, March 4, 1970, abandoned.

[52] U.S. Cl. ............................ 260/521 B; 423/520; 423/545
[51] Int. Cl.² .................. C07C 51/00; C07C 37/10
[58] Field of Search .................... 260/621 M, 521 B

[56] References Cited

UNITED STATES PATENTS

| | | | |
|---|---|---|---|
| 2,669,580 | 2/1954 | Long et al. | 260/521 B |
| 2,669,581 | 2/1954 | Scalera et al. | 260/521 B |
| 3,862,245 | 1/1975 | Greco | 260/621 M |
| 3,862,246 | 1/1975 | Greco | 260/621 M |

*Primary Examiner*—Norman Morgenstern
*Attorney, Agent, or Firm*—Oscar B. Brumback; Herbert J. Zeh, Jr.

[57] ABSTRACT

Alpha-resorcylic acid is produced by the hydrolysis of 3,5-diamino benzoic acid in an aqueous solution of ammonium bisulfate. The reactants are contacted at an elevated temperature for a period of time sufficient to hydrolyze the 3,5-diamino benzoic acid to alpha-resorcylic acid and the alpha-resorcylic acid so produced is separated from the reaction mixture. The ammonium sulfate is regenerated to ammonium bisulfate by removing the water and thermally decomposing the by-product ammonium sulfate at an elevated temperature.

3 Claims, No Drawings

HYDROLYSIS OF 3,5-DIAMINO BENZOIC ACID TO PRODUCE ALPHA-RESORCYLIC ACID

CROSS REFERENCE TO RELATED APPLICATIONS

This application is a continuation-in-part of my copending application Ser No. 267,525 filed June 29, 1972, now U.S. Pat. No. 3,862,246, which, in turn, is a continuation-in-part of application Ser. No. 16,545 filed Mar. 4, 1970 now abandoned.

BACKGROUND OF THE INVENTION

This invention relates to the production of alpha-resorcylic acid and more particularly to the hydrolysis of 3,5-diamino benzoic acid with ammonium bisulfate to produce alpha-resorcylic acid.

Alpha-resorcylic acid (3,5-dihydroxy benzoic acid) is generally in the form of white crystals with a melting point of 237°C. Alpha-resorcylic acid is used as an intermediate for dyes, in pharmaceuticals, as a light stabilizer and in resins. It is used, for example, as an ultraviolet absorber in the formulation of suntan lotions.

SUMMARY OF THE INVENTION

In accordance with this invention, alpha-resorcylic acid is made by the ammonium bisulfate hydrolysis of 3,5-diamino benzoic acid by contacting the 3,5-diamino benzoic acid with at least 4 but preferably 6 moles of ammonium bisulfate per mole of the 3,5-diamino benzoic acid in aqueous solution at a temperature of about 200°–300°C, but preferably 220°C, for a time sufficient to hydrolyze the 3,5-diamino benzoic acid to alpha-resorcylic acid. The reaction may be expressed as

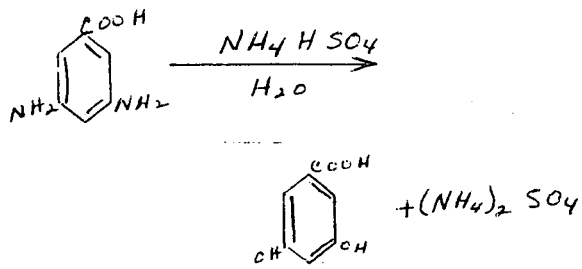

The aqueous solution is then cooled and the product alpha-resorcylic acid extracted using a suitable inert solvent. Hydrolysis may be repeated by reheating the reaction mixture after extraction and the ammonium sulfate can be regenerated for reuse in the reaction by evaporating the water and heating the melt of the mixed ammonium sulfates at a temperature of 310°–450°C. Upon cooling the resulting ammonium bisulfate is dissolved in water, adjusted to the desired concentration and recycled to the reaction zone. The solvent solution from the extraction step is evaporated to give the alpha-resorcylic acid in substantially pure form.

DETAILED DESCRIPTION

In accordance with this invention, 3,5-diamino benzoic acid is hydrolyzed in an aqueous medium through the use of ammonium bisulfate to produce alpha-resorcylic acid. The by-product salt can be regenerated to ammonium bisulfate for reuse in the process.

The composition of the hydrolysis medium is of particular importance. A minimum of 4 but preferably 6 moles of ammonium bisulfate, based on the number of moles of 3.5-diamino benzoic acid, is necessary in order to provide a reasonable yield of alpha-resorcylic acid in a single hydrolysis reaction. The hydrolysis can be carried out in one step or it can be continued sequentially by terminating the reaction, cooling, extracting the product and reheating the hydrolysis mixture without further addition of reactants. A one-step hydrolysis is desirable from the standpoint of ease and efficiency of operation, although an increase in yield can be achieved by a second hydrolysis of the reaction mixture after removing the product from the first hydrolysis. From the standpoint of obtaining high yields in a single hydrolysis step, the use of high concentrations of ammonium bisulfate up to the point of saturation of the aqueous solution is desirable. With high concentrations, a practical problem arises in the handling of large quantities of salt.

Water must be present in an amount sufficient to provide for hydrolysis and also to serve as a diluent or solvent for the 3,5-diamino benzoic acid, ammonium bisulfate and the ammonium sulfate formed during the course of the reaction. At least 40 but preferably 60 moles of water per mole of 3,5-diamino benzoic acid must be present to dissolve sufficient quantities of ammonium bisulfate. As the amount of ammonium bisulfate is increased, more water, up to about 120 moles, is required. The use of excess water results in a practical problem of water removal during the ammonium bisulfate regeneration step.

The reaction temperature can vary over a wide range between about 200° to 300°C. At temperatures below about 200°C. an unduly long reaction time is required and the yields are generally low. As the temperature is increased the pressure must be correspondingly increased to maintain the reaction solution in the aqueous phase. At temperatures as high as 300°C., a steam pressure of up to about 1500 psig is required for this purpose and there is some danger of resin formation if the contact time is too long. No advantage is obtained by increasing or decreasing the pressure to a value other than that sufficient to provide for a liquid reaction medium. To avoid the use of considerable pressure, with the corresponding equipment requirements, temperatures in the range of 220°–260°C. are preferred.

The reaction time or contact time varies primarily with the temperature and to a lesser extent with the mole ratio of the reactants. At a minimum temperature, e.g., 200°C., a per pass reaction time of 8 hours is ordinarily required. At 220°C. effective results from the standpoint of yield are obtained using a two pass hydrolysis reaction and a reaction time of 6 to 7 hours per pass. Also at 220°C. good results are obtained in a single pass hydrolysis step if the reaction time is extended to about 13 hours. At temperatures about 250°C., hydrolysis can occur in 5 minutes to a half hour. From a practical standpoint an overall per pass hydrolysis time can be considered to be from 5 minutes to 13 hours.

Hydrolysis is carried out in a zone which is resistant to any substantial attack by the ammonium bisulfate or the 3,5-diamino benzoic acid. At very low temperatures within the useful range, an ordinary glass lined Pfaudler kettle can be used. When higher temperatures are required, other construction materials become necessary. At temperatures up to 220°–230°C. Teflon lined reactors are effective. Higher temperature ranges require the use of more durable equipment, such as tantalum lined reactors.

After the period of hydrolysis, the reaction mixture is cooled to prevent resinification of the product in the acidic aqueous reaction mixture and to enable the separation of the by-product by organic solvent extraction. Any substantially water-immiscible solvent which will dissolve the alpha-resorcylic acid is useful. Ethyl ether is the preferred solvent. The organic solvent phase is then separated from the reaction mixture by decantation and the alpha-resorcylic acid is removed from the solvent by evaporation of the solvent.

After removal of the alpha-resorcylic acid, the resulting aqueous reaction mixture can be reheated to the hydrolysis temperature for a second or even a third hydrolysis step. The second and subsequent hydrolysis steps are carried out as before by heating the reaction mixture to the appropriate temperature of hydrolysis for the desired period of time, cooling and removing the alpha-resorcylic acid product by solvent extraction.

Ammonium sulfate by-product is regenerated to ammonium bisulfate for reuse in the process by removing the residual water from the remaining reaction mixture and heating the molten salt, primarily mixed ammonium sulfate, and ammonium bisulfate at atmospheric pressure at a temperature between 310°–450°C. At temperatures below 310°C., an unduly long time is required to effect decomposition. No practical advantages are seen in using temperatures higher than 450°C. and above this temperature the bisulfate tends to decompose. At 330°C., 75–95 percent of the ammonium sulfate is converted in a few minutes to ammonium bisulfate. Slightly higher conversions are obtained at higher temperatures although this advantage is offset by the increased equipment cost required. During the decomposition of the ammonium sulfate, residual organic materials may be pyrolyzed to black granules resembling activated charcoal. This charcoal-like material is easily removed by dissolving the mixture of ammonium sulfate and ammonium bisulfate product in water followed by a filtration step. The ammonia formed during the decomposition can be recovered and used in other chemical processes. The clear, filtered salt solution, the salt portion of which 75–95 percent ammonium bisulfate, is adjusted to the desired concentration and is recycled to the reaction mixture for hydrolysis of additional 3,5-diamino benzoic acid.

My invention is further illustrated by the following example.

A solution of 3,5-diamino benzoic acid (33 g., 0.18 moles) of 90% purity, ammonium bisulfate (138 g., 1.2 moles) and water (216 g., 12 moles) was heated to 220°C. for 6–7 hours. The amber colored reaction mixture was cooled, was filtered, and was shaken with ether (2 × 200 ml) for two extractions. The aqueous solution after boiling to remove dissolved ether was heated again for 6–7 more hours at 220°C. for another hydrolysis. The reaction mixture was cooled and was extracted twice with ethyl ether (2 × 250 ml).

The ether extraction solutions were stripped to dryness on a steam bath and the white, crystalline, substantially pure alpha-resorcylic acid remained. The first ether extract gave 8 g. and the second ether extract gave 9 g. of alpha-resorcylic acid for a total yield of 61%.

The aqueous reaction medium remaining after the ether extractions was decomposed to provide bisulfate for recycling as the hydrolyzing agent. To this end, the aqueous medium is heated and the inorganic sulfates present after evaporating the medium to a dry salt weighed 144 g. An aliquot of the salt was titrated with 1/10 N NaOH in the presence of brom cresol blue indicator and was found to be 87% bisulfate (13% ammonium sulfate by difference). This mixed, dry salt was heated in an oil bath and could be stirred easily after reaching 146°C. which is the melting point of ammonium bisulfate. At 298°C. for 2 min., the salt weighed 142.4 g. and was 70% ammonium bisulfate by titration. Heating was continued until a temperature of 312°C. was reached and the melt was held at 312°C. for 12 minutes, at which time the ammonium bisulfate content was 95%; the salt weighed 141 g. (theoretical weight loss). The loss in weight of the salt on heating was due to ammonia evolution. The organic material in the medium was converted to fine carbonaceous particles during the heating of the melt. The thermally treated salt mixture was taken up in water and the black mixture filtered. After filtering, the ammonium bisulfate solution was clear. Evaporation of the filtrate gave light yellow ammonium bisulfate crystals. These crystals can be used for further hydrolyzing of 3,5-diamino benzoic acid.

The foregoing has presented a simple and effective process for the production of alpha-resorcylic acid.

What is claimed is:

1. A method of making alpha-resorcylic acid comprising:
   a. contacting 3,5-diamino benzoic acid with ammonium bisulfate in an aqueous solution that contains 4 to 12 moles of ammonium bisulfate per mole of 3,5-diamino benzoic acid and 40 to 120 moles of water per mole of 3,5-diamino benzoic acid and that is at a temperature of 200° to 300°C. for a period of ½ to 13 hours to hydrolyze said 3,5-diamino benzoic acid to alpha-resorcylic acid,
   b. cooling said hydrolysis reaction mixture, and
   c. extracting said alpha-resorcylic acid from said solution with a water-immiscible organic solvent.

2. The method of claim 1 wherein the solution from which the alpha-resorcylic acid has been extracted is again maintained at a temperature of 200° to 300°C. for an additional period of time to hydrolyze residual 3,5-diamino benzoic acid to alpha-resorcylic acid.

3. A method of making alpha-resorcylic acid comprising:
   a. contacting 3,5-diamino benzoic acid with ammonium bisulfate in an aqueous solution that contains 4 to 12 moles of ammonium bisulfate per mole of said 3,5-diamino benzoic acid and 40 to 120 moles of water per mole of said 3,5-diamino benzoic acid and that is at a temperature of 200° to 300°C. for a period of ½ to 13 hours to hydrolyze said 3,5-diamino benzoic acid to alpha-resorcylic acid,
   b. cooling said hydrolysis reaction mixture,
   c. extracting said alpha-resorcylic acid from said solution with an inert water-immiscible organic solvent, thereafter
   d. evaporating the water from said solution to obtain a residue consisting essentially of ammonium sulfate and ammonium bisulfate, and
   e. heating said residue to an elevated temperature of 210° to 450°C. to convert said ammonium sulfate to ammonium bisulfate for reuse to hydrolyze more of said 3,5-diamino benzoic acid to alpha-resorcylic acid.

\* \* \* \* \*